(12) United States Patent
Smischney et al.

(10) Patent No.: US 11,357,743 B2
(45) Date of Patent: Jun. 14, 2022

(54) KETAMINE AND PROPOFOL ADMIXTURE

(71) Applicants: Mayo Foundation for Medical Education and Research, Rochester, MN (US); Regents of the University of Minnesota, Minneapolis, MN (US)

(72) Inventors: Nathan J. Smischney, Rochester, MN (US); Wayne T. Nicholson, Rochester, MN (US); Jayanth Panyam, Plymouth, MN (US)

(73) Assignees: Mayo Foundation for Medical Education and Research, Rochester, MN (US); Regents of the University of Minnesota, Minneapolis, MN (US)

( * ) Notice: Subject to any disclaimer, the term of this patent is extended or adjusted under 35 U.S.C. 154(b) by 127 days.

(21) Appl. No.: 16/606,056

(22) PCT Filed: Apr. 19, 2018

(86) PCT No.: PCT/US2018/028325
§ 371 (c)(1),
(2) Date: Oct. 17, 2019

(87) PCT Pub. No.: WO2018/195292
PCT Pub. Date: Oct. 25, 2018

(65) Prior Publication Data
US 2021/0137851 A1    May 13, 2021

Related U.S. Application Data

(60) Provisional application No. 62/487,330, filed on Apr. 19, 2017.

(51) Int. Cl.
| | | |
|---|---|---|
| *A61K 31/135* | (2006.01) | |
| *A61K 31/05* | (2006.01) | |
| *A61P 23/00* | (2006.01) | |
| *A61K 9/00* | (2006.01) | |
| *A61K 9/107* | (2006.01) | |
| *A61K 47/44* | (2017.01) | |

(52) U.S. Cl.
CPC .......... *A61K 31/135* (2013.01); *A61K 9/0019* (2013.01); *A61K 9/107* (2013.01); *A61K 31/05* (2013.01); *A61K 47/44* (2013.01); *A61P 23/00* (2018.01)

(58) Field of Classification Search
None
See application file for complete search history.

(56) References Cited

U.S. PATENT DOCUMENTS

| | | |
|---|---|---|
| 5,714,520 A | 2/1998 | Jones et al. |
| 8,476,010 B2 | 7/2013 | Desai et al. |
| 2012/0009243 A1 | 1/2012 | Vikbjerg et al. |
| 2013/0158016 A1 | 6/2013 | Enrique |

FOREIGN PATENT DOCUMENTS

| | | | |
|---|---|---|---|
| WO | WO 2004/108113 | 12/2004 | |
| WO | WO 2017/017693 | 2/2017 | |
| WO | WO2017017693 | * 2/2017 | |

OTHER PUBLICATIONS

Amornyotin, "Ketofol: A Combination of Ketamine and Propofol," J. Anesth. Crit. Care Open Access, Nov. 18, 2014, 1(5):00031, 3 pages.
Arora, "Combining Ketamine and Propofol ("Ketofol") for Emergency Department Procedural Sedation and Analgesia: A Review," West. J. Emerg. Medicine, Jan. 2008, 9(1):20-23.
Baker et al., "Propofol: The Challenges of Formulation," Anesthesiology, Oct. 2005, 103(4):860-876.
EP Extended European Search Report in European Appln. No. 18788507.4, dated Mar. 31, 2020, 8 pages.
fda.gov [online], "Diprivan," dated Feb. 2014, retrieved on Oct. 23, 2020, retrieved from URL <https://www.accessdata.fda.gov/drugsatfda_docs/label/2014/019627s0621b1.pdf>, 51 pages.
Felfernig et al., "Postoperative Vigilance in Patients with Total Intravenous Anaesthesia with Ketamine/Propofol," J. R. Nav. Med. Service, 2006, 92(2):64-68.
Hui et al., "Additive Interactions between Propofol and Ketamine When Used for Anesthesia Induction in Female Patients," Anesthesiology, Mar. 1995, 82(3):641-648.
Metselaar et al., "Liposomes for intravenous drug targeting: design and applications," Mini Rev. Med. Chemistry, Aug. 2002, 2(4):319-329.
Park et al., "The Effect of Lidocaine on the Globule Size Distribution of Propofol Emulsions," Anesth. Analgesia, Sep. 2003, 97(3):769-771.
PCT International Preliminary Report on Patentability in International Appln. No. PCT/US2018/028325, dated Oct. 31, 2019, 6 pages.
PCT International Search Report and Written Opinion in International Appln. No. PCT/US2018/028325, dated Jun. 20, 2018, 13 pages.
Smischney et al., ""Ketofol" may be associated with better pain control and without increased risk of nausea and vomiting," Poster presented at the American Society Anesthesiologists Annual Meeting, Oct. 15, 2011, Chicago, Illinois, USA, 1 page.
Smischney et al., "Ketamine/propofol admixture (ketofol) is associated with improved hemodynamics as an induction agent: A randomized, controlled trial," J. Trauma Acute Care Surgery, Jul. 2012, 73(1):94-101.
Tsur et al., "Hypersensitivity associated with sugammadex administration: a systematic review," Anaesthesia, May 22, 2014, 69(11):1251-1257.
utexas.edu [online], ""Ketofol" for Procedural Sedation and Analgesia in the Emergency Department: Is the Juice Worth the Squeeze?," dated Sep. 5, 2014, retrieved on Oct. 23, 2020, retrieved from URL <http://sites.utexas.edu/pharmacotherapy-rounds/files/2015/09/fowler09-04-14.pdf>, 20 pages.
White, "Clinical Pharmacology of Intravenous Induction Drugs," Int. Anesthesiol. Clinics, Jul. 1988, 26(2):98-104.

(Continued)

*Primary Examiner* — Shengjun Wang
(74) *Attorney, Agent, or Firm* — Fish & Richardson P.C.

(57) ABSTRACT

Pharmaceutical formulations comprising ketamine, propofol, and a lipid are provided. Methods of making the formulations and methods of using the formulations to (Continued)

provide sedation, amnesia, analgesia, anxiolysis, and/or stable hemodynamics are also provided.

11 Claims, No Drawings

(56) References Cited

OTHER PUBLICATIONS

Willman et al., "A Prospective Evaluation of "Ketofol" (Ketamine/Propofol Combination) for Procedural Sedation and Analgesia in the Emergeney Department," Ann. Emerg. Medicine, Jan. 2007, 49(1):23-30.

* cited by examiner

KETAMINE AND PROPOFOL ADMIXTURE

CLAIM OF PRIORITY

This application is a National Stage application under 35 U.S.C. § 371 of International Application No. PCT/US2018/028325, having an International Filing Date of Apr. 19, 2018, which claims the benefit of U.S. Provisional Application No. 62/487,330, filed on Apr. 19, 2017. The entire contents of the foregoing are hereby incorporated by reference.

TECHNICAL FIELD

This invention relates to pharmaceutical formulations comprising ketamine and propofol.

BACKGROUND

Critically ill patients often require urgent and/or emergent intubations for diagnostic and/or therapeutic interventions. Preparation and administration of sedation for intubations is of vital importance, especially in the critically ill population where many patients have multiple co-morbidities. Etomidate is a medication that was developed to afford hemodynamic stability during this process. Etomidate, however, has been associated with adrenal suppression and may be associated with increased mortality among critically ill patients.

SUMMARY

An admixture of ketamine and propofol (referred to as "ketofol") has shown hemodynamic stability, similar to etomidate, but based on the balancing of the hemodynamic effects of the two individual agents. Current preparations of ketofol generally involve mixing a saline solution of the hydrochloride salt of ketamine with a lipid emulsion of propofol just prior to administration (see, e.g., West J Emerg Med. 2008 January; 9(1): 20-23). The requirement for mixing immediately prior to administration can cause delays in administration of the drug and subsequent procedures Further, the addition of another solution (such as a lidocaine solution) to a propofol lipid emulsion can also increase the occurrence of lipid emulsion crackingan/or emulsion instability (see, e.g., Anesth Analg. 2003 September; 97(3):769-71). While attempts have been made to produce pre-mixed formulations of analgesics combined with propofol (see, e.g., WO/2004/108113), such formulations complex the propofol to cyclodextrin, thereby removing propofol from the lipid phase and introducing the potential toxic effects of cyclodextrin (see, e.g., Anaesthesia. 2014 November; 69(11):1251-7). There remains a need for stable pre-made formulations comprising ketamine and propofol, including sterile formulations with long-term stability.

Provided herein are pharmaceutical formulations comprising ketamine, propofol, and a lipid, wherein the ketamine is substantially dissolved in the lipid. The formulation can be an oil-in-water emulsion. In some embodiments, the formulation can be essentially free of chloride ions. The formulations can comprise from about 2.5% (w/v) to about 20% (w/v) lipid, about 1 mg/ml to about 10 mg/ml ketamine, and about 1 mg/ml to about 10 mg/ml propofol. The ratio of ketamine to propofol can range from about 1:4 to about 2:1. The lipid can be selected from soybean oil, purified egg phospholipid, oleic acid, glyceryl esters and mixtures thereof. In some embodiments, the formulation can be stable for about one month, about two months, about five months, about six months, about one year, about eighteen months, or about two years. In some embodiments, the emulsion formulations comprising ketamine and propofol maintain emulsion droplet size distribution and phase stability for at least about one year, at least about eighteen months, or at least about two years. In some embodiments, the emulsion formulations maintain phase stability for at least about one year, at least about eighteen months, or at least about two years. In some embodiments, the emulsion formulations maintain emulsion droplet size distribution for at least two years.

In another aspect, methods of manufacturing pharmaceutical formulations comprising ketamine and propofol are provided. For example, the method can include dissolving ketamine in an oil phase to produce an emulsion formulation comprising ketamine and propofol. The ketamine can be free base ketamine. The method can further comprise dissolving propofol in the oil phase. In some implementations, propofol is present in the oil phase prior to the dissolving the ketamine in the oil phase. In other implementations, ketamine is dissolved in the oil phase prior to dissolving the propofol in the oil phase. The method can further comprise adding a surfactant. In some embodiments, the formulations can be essentially free of chloride ions.

In another aspect, oil-in-water emulsions comprising ketamine, propofol, and a lipid are provided, wherein the emulsions are essentially free of chloride ions. The emulsions can comprise about 10% (w/v) lipid. The ketamine can be present in a concentration of from about 2 mg/ml to about 5 mg/ml. The propofol can be present in a concentration of from about 5 mg/ml to about 8 mg/ml.

Another aspect of the disclosure provides a pharmaceutical composition prepared by a process comprising dissolving ketamine in an oil phase to produce an emulsion formulation comprising ketamine and propofol.

A method of providing sedation, amnesia, analgesia, anxiolysis, hemodynamic stability, or combinations thereof to a subject is also provided herein, comprising administering a pharmaceutical formulation described herein to the subject. In some aspects, the administering comprises injecting the formulation into the subject.

The compositions described in this disclosure provide several advantages. Stable pre-mixed, ready-to-use formulations of ketamine and propofol may reduce errors and delays in administration associated with either mixing ketamine and propofol just prior to administration or administering the two compounds separately, and may conserve medical supplies and decrease the likelihood of bacterial contamination. The pre-mixed formulations of ketamine and propofol described herein can enhance the safety of "ketofol" administration due to stable emulsion droplet size distribution and/or phase stability. Ketamine may be a potent alternate pain medication for patients refractory to opioids. If practitioners can choose a pre-mixed formulation of ketamine and propofol, ketamine may be available to administer to patients in place of narcotics such as opioids, thereby avoiding side effects associated with narcotics. The simultaneous administration of benzodiazepines with ketamine, and the potential negative side effects of benzodiazepines, may also be avoided, since simultaneous administration of propofol may lessen the emergence phenomenon associated with ketamine.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

For the terms "for example" and "such as," and grammatical equivalences thereof, the phrase "and without limitation" is understood to follow unless explicitly stated otherwise. As used herein, the term "about" is meant to account for variations due to experimental error. As used herein, the singular forms "a," "an," and "the" are used interchangeably and include plural referents unless the context clearly dictates otherwise.

Also herein, the recitations of numerical ranges by endpoints include all numbers subsumed within that range (e.g., 1 to 5 includes 1, 1.5, 2, 2.75, 3, 3.80, 4, 5, etc.).

Other features and advantages of the invention will be apparent from the following detailed description and figures, and from the claims.

DETAILED DESCRIPTION

The present disclosure is directed to stable pre-made formulations comprising ketamine and propofol that can be administered to subjects, in some embodiments via injection, and can provide sedation, amnesia, analgesia, anxiolysis, and/or hemodynamic stability. In some embodiments, the formulations described herein exhibit a high degree of emulsion stability and resistance to bacterial contamination.

In general, the formulations of the present disclosure comprise ketamine, propofol, and a lipid. In some embodiments, the formulations further comprise water or saline.

Ketamine free base, or (±)-2-(2-chlorophenyl)-2-(methylamino) cyclohexanone, can be used in the formulations herein, as well as other forms of ketamine, such as S-Ketamine (active enantiomer).

The ketamine used in the formulations described herein can be present at any concentration. In some embodiments, the ketamine is present in a concentration of from about 1 mg/ml to about 100 mg/ml. For example, the ketamine can be present in a concentration from about 1 mg/ml to about 70 mg/ml, about 1 mg/ml to about 50 mg/ml, about 1 mg/ml to about 20 mg/ml, about 1 mg/ml to about 10 mg/ml, or about 2 mg/ml to about 5 mg/ml. In some embodiments, the ketamine is present in a concentration of about 2 mg/ml, about 2.5 mg/ml, about 3.3 mg/ml, or about 5 mg/ml.

Propofol, or 2,6-diisopropylphenol, can also be present in the formulations described herein in any concentration. The propofol is formulated in a lipid emulsion and in some embodiments is substantially dissolved in the lipid phase of the formulations. In some embodiments, the propofol is present in a concentration of from about 1 mg/ml to about 10 mg/ml. For example, the propofol is present in a concentration from about 5 mg/ml to about 8 mg/ml. In some embodiments, the propofol is present in a concentration of about 5 mg/ml, about 6.6 mg/ml, about 7.5 mg/ml, or about 8 mg/ml.

The ketamine and propofol can each be present in a range of concentrations, with lower limits based on minimum therapeutic potency of the ketamine or propofol, and upper limits based primarily on solubility and/or safety of each of the drugs. The ratio of ketamine to propofol in the formulations described herein can range from about 1:4 to about 2:1. In some embodiments of the formulations, the ratio of ketamine to propofol can range from about 1:4 to about 1:1. In some embodiments, the ratio of ketamine to propofol is selected from about 1:4, about 1:3, about 1:2, about 1:1, and about 2:1. Exemplary concentrations of ketamine and propofol in the formulations described herein include about 6.6 mg/ml ketamine with about 3.3 mg/ml propofol, about 5 mg/ml ketamine with about 5 mg/ml propofol, about 3.3 mg/ml ketamine with about 6.6 mg/ml propofol, about 2.5 mg/ml ketamine with about 7.5 mg/ml propofol, and about 2 mg/ml ketamine with about 8 mg/ml propofol.

The formulations provided herein generally comprise oil-in-water emulsions and the oil phase of the emulsions comprises a lipid. In some embodiments, the formulations described herein comprise from about 2.5% (w/v) to about 20% (w/v) lipid. In some embodiments, a formulation can comprise from about 5% to about 15% lipid. In some embodiments, a formulation can comprise from about 9% to about 11% lipid. In some embodiments, a formulation can comprise from about 9.5% to about 10.5% lipid. In some embodiments, a formulation comprises about 10% lipid. The lipid used in the formulations described herein can be pharmaceutical grade in some embodiments. Exemplary lipids useful in the formulations of described herein include soybean oil, purified egg yolk phospholipids, and mixtures thereof. In some embodiments, the lipid is soybean oil. In another exemplary embodiment, the lipid phase can include 10% (w/v) soybean oil and 1.2% (w/v) purified egg phospholipid.

An exemplary formulation described herein contains 10% (w/v) to 20% (w/v) soybean oil, as well as glycerol, purified egg yolk phospholipids, oleic acid, disodium edetate, and enough sodium hydroxide to adjust the pH to a desired range. In some embodiments, the pH of the formulation can be adjusted with sodium hydroxide or other suitable pH modifier. In some embodiments, the pH of the formulation can be from about pH 7.0 to pH 9, from about pH 7.0 to about pH 8.5, from about pH 7.0 to about pH 7.5, from about pH 7.5 to about pH 8.5, from about pH 7.5 to about pH 8.0, from about pH 8.0 to about pH 8.5, from about pH 7.5 to about pH 9.0, from about pH 8.0 to about pH 9.0 from about pH 8.5 to pH 9.0. Another exemplary formulation described herein contains 10% (w/v) soybean oil, as well as 2.25% (w/v) glycerol, 1.2% (w/v) purified egg yolk phospholipids, oleic acid, disodium edetate, and enough sodium hydroxide to adjust the pH to a range of from about 7.0 to 8.5.

In one exemplary embodiment, the formulation comprises ketamine and propofol, with pH adjusted to about 7.0. In one exemplary embodiment, the formulation comprises ketamine and propofol, with pH adjusted to about 7.5. In one exemplary embodiment, the formulation comprises ketamine and propofol, with pH adjusted to about 8.0. In one exemplary embodiment, the formulation comprises ketamine and propofol, with pH adjusted to about 8.5. In one exemplary embodiment, the formulation comprises ketamine and propofol, with pH adjusted to about 9.0.

In some embodiments of the formulations described herein, the ketamine is present in the lipid, and is therefore present in the oil phase of the emulsions. In some embodiments, the propofol is also present in the lipid, and is therefore present in the oil phase of the emulsions. As used herein, "present in the lipid" means that at least about 70 wt.-%, at least 80 wt.-%, at least 90 wt.-%, at least 95 wt.-%, at least 96 wt.-%, at least 97 wt.-%, at least 98 wt.-%, at least 99 wt.-%, or 100 wt.-% of the ketamine and/or propofol is dispersed, suspended, or dissolved in the lipid and/or oil phase of the formulations at temperatures ranging from 4° C. to 25° C. and 1 atm pressure.

In some embodiments, a formulation comprises ketamine and propofol, and at least 70% of the ketamine is present in the lipid and/or oil phase. In some embodiments, a formulation comprises ketamine and propofol, and at least 80% of the ketamine is present in the lipid and/or oil phase. In some embodiments, a formulation comprises ketamine and propofol, and at least 90% of the ketamine is present in the lipid and/or oil phase. In some embodiments, a formulation comprises ketamine and propofol, and at least 95% of the ketamine is present in the lipid and/or oil phase. In some embodiments, a formulation comprises ketamine and propofol, and at least 97% of the ketamine is present in the lipid and/or oil phase. In some embodiments, a formulation comprises ketamine and propofol, and at least 99% of the ketamine is present in the lipid and/or oil phase. In some embodiments, a formulation comprises ketamine and propofol, and at least 99.5% of the ketamine is present in the lipid and/or oil phase. In some embodiments, a formulation comprises ketamine and propofol, and at least 99.9% of the ketamine is present in the lipid and/or oil phase.

In some embodiments, a formulation comprises ketamine and propofol, and at least 70% of the propofol is present in the lipid and/or oil phase. In some embodiments, a formulation comprises ketamine and propofol, and at least 80% of the propofol is present in the lipid and/or oil phase. In some embodiments, a formulation comprises ketamine and propofol, and at least 90% of the propofol is present in the lipid and/or oil phase. In some embodiments, a formulation comprises ketamine and propofol, and at least 95% of the propofol is present in the lipid and/or oil phase. In some embodiments, a formulation comprises ketamine and propofol, and at least 97% of the propofol is present in the lipid and/or oil phase. In some embodiments, a formulation comprises ketamine and propofol, and at least 99% of the propofol is present in the lipid and/or oil phase. In some embodiments, a formulation comprises ketamine and propofol, and at least 99.5% of the propofol is present in the lipid and/or oil phase. In some embodiments, a formulation comprises ketamine and propofol, and at least 99.9% of the propofol is present in the lipid and/or oil phase.

In some embodiments of the formulations described herein, the ketamine is substantially dissolved in the lipid, and is therefore substantially dissolved in the oil phase of the emulsions. In some embodiments, the propofol is also substantially dissolved in the lipid, and is therefore substantially dissolved in the oil phase of the emulsions. As used herein, "substantially dissolved" means that at least about 70 wt.-%, at least 80 wt.-%, at least 90 wt.-%, at least 95 wt.-%, at least 96 wt.-%, at least 97 wt.-%, at least 98 wt.-%, at least 99 wt.-%, or 100 wt.-% of the ketamine and/or propofol is dissolved in the lipid and/or oil phase of the formulations at temperatures ranging from 4° C. to 25° C. and 1 atm pressure.

The formulations described herein are stable emulsions. As used herein, "stable" means that the emulsions maintain phase stability. In some embodiments, a stable emulsion does not separate into distinct oil and water phases upon standing at 4° C. to 22° C. or at 4° C. to 25° C. for at least two months. For example, in some embodiments described herein, the formulations exhibit an acceptable shelf life for commercial use, e.g., in some embodiments, the formulations remain stable, maintain emulsion droplet size distribution and/or do not separate into distinct oil and water phases upon standing for up to 2 months, up to 6 months, up to 1 year, up to 2 years, up to 3 years, and the like at temperatures ranging from 4° C. to 25° C.

Because the formulations described herein are stable enough to provide a pre-mixed formulation of ketamine and propofol, the ketamine and propofol can be drawn from a single pre-mixed vial rather than being mixed just prior to administration. The formulations can also avoid potential risks associated with cracking the propofol/soybean oil emulsion, such as development of micro-emboli, that can occur in the conventional procedures involving mixing a saline solution of the hydrochloride salt of ketamine with a lipid emulsion of propofol prior to administration. The stable pre-mixed formulations can also provide a reduction in dosing errors and other drug errors that occur when clinicians attempt to mix ketamine/propofol formulations in clinical settings.

The reduction in delayed administration provided by the formulations described herein may allow practitioners to save time in an emergent situation rather than mixing the two medications up at the patient's bedside. The availability of premixed ketamine and propofol formulations as described herein further gives practitioners an option to choose ketamine over administration of other pain medications such as narcotics and benzodiazepines, thereby reducing the side-effects associated with administration of these painkillers, including delirium associated with benzodiazepine administration, and hemodynamic instability. Additionally, ketamine preserves airway reflexes and doesn't depress the respiratory drive to the same degree as narcotics or larger doses of propofol alone. When ketamine and propofol are used together as a formulation, less propofol is used and narcotics may be avoided thereby lessening respiratory depression. Ketamine also increases heart rate and blood pressure thus attenuating the depressive effects of propofol on heart rate and blood pressure. Therefore, administration of the formulations described herein may allow improved maintenance of respiratory drive during anesthesia and provide stable blood pressure and heart rate during anesthesia.

Additionally, since the formulations described herein allow the ketamine and propofol to be drawn from a single pre-mixed vial, risks of potential bacterial contamination of the carbon, hydrogen, and nitrogen rich propofol stock formulations used to mix with ketamine in the operating rooms are reduced.

In some embodiments, the formulations comprising ketamine and propofol are essentially free of chloride ion. As used herein, "essentially free" of chloride ion means that the composition includes less than 0.02% (w/v), less than 0.01% (w/v), less than 0.005% (w/v), less than 0.001% (w/v), less than 0.0005% (w/v), or less than 0.0001% (w/v) chloride ion weight/volume (g/mL), or less than 1%, less than 0.1%, less than 0.01%, less than 0.05%, less than 0.001%, less than 0.0005%, or less than 0.0001% by weight chloride ion. In some embodiments, an exemplary formulation comprises ketamine, propofol, and less than 0.02% (w/v) chloride ion. In some embodiments, an exemplary formulation comprises ketamine, propofol, and less than 0.01% (w/v) chloride ion. In some embodiments, an exemplary formulation comprises ketamine, propofol, and less than 0.005% (w/v) chloride ion. In some embodiments, an exemplary formulation comprises ketamine, propofol, and less than 0.001% (w/v) chloride ion. In some embodiments, an exemplary formulation comprises ketamine, propofol, and less than 0.0005% (w/v) chloride ion. In some embodiments, an exemplary formulation comprises ketamine, propofol, and less than 0.0001% (w/v) chloride ion.

In some embodiments, formulations essentially free of chloride ion can generate highly stable oil-in-water emulsions with ketamine free base dissolved in the oil phase. In some embodiments, non-saline aqueous phase (e.g., deionized water) can be used to in the formulations.

An exemplary pharmaceutical formulation as described herein comprises about 10% (w/v) soybean oil, about 5 mg/ml free base ketamine, and about 5 mg/ml propofol. Another exemplary pharmaceutical formulation provided herein comprises about 10% (w/v) soybean oil, about 3.3 mg/ml free base ketamine, and about 6.6 mg/ml propofol. Other exemplary pharmaceutical formulations provided herein comprise about 10% (w/v) soybean oil, about 2.5 mg/ml free base ketamine, and about 7.5 mg/ml propofol, or about 10% (w/v) soybean oil, about 2 mg/ml free base ketamine, and about 8 mg/ml propofol. In some embodiments, a formulation can comprise from about 1 mg/ml to about 6 mg/ml ketamine, from about 4 mg/ml to about 10 mg/ml propofol, and from about 9% (w/v) to about 11% (w/v) lipid. In some embodiments, a formulation can comprise from about 2 mg/ml to about 5 mg/ml ketamine, from about 5 mg/ml to about 8 mg/ml propofol, and from about 9.5% (w/v) to about 10.5% (w/v) lipid. In other embodiments, a formulation can comprise from about 3 mg/ml to about 5 mg/ml ketamine, from about 5 mg/ml to about 7 mg/ml propofol, and from about 9.5% (w/v) to about 10.5% (w/v) lipid.

In some embodiments, a formulation can comprise ketamine, propofol and at least 10% (w/v) lipid. In some embodiments, a formulation can comprise ketamine, propofol, at least 10% (w/v) soybean oil. In some embodiments, a formulation can comprise ketamine, propofol, at least 10% (w/v) soybean oil and less than 0.02% (w/v) chloride ion. In some embodiments, a formulation can have a pH adjusted to about 7.5 and can comprise ketamine, propofol, at least 10% (w/v) soybean oil, and less than 0.01% (w/v) chloride ion. In some embodiments, a formulation can comprise ketamine, propofol, at least 10% (w/v) soybean oil, and less than 0.01% (w/v) chloride ion and have a pH adjusted to about 8.5. In some embodiments, a formulation can comprise ketamine, propofol, and at least 10% (w/v) soybean oil, wherein at least 90% of ketamine is in the lipid. In some embodiments, a formulation can comprise ketamine, propofol, and at least 10% (w/v) soybean oil, wherein at least 95% of ketamine is in the lipid. In some embodiments, a formulation can comprise ketamine, propofol, and at least 10% (w/v) soybean oil, wherein at least 97% of ketamine is in the lipid. In some embodiments, a formulation can comprise ketamine, propofol, and at least 10% (w/v) soybean oil, wherein at least 99% of ketamine is in the lipid.

In some embodiments, the pharmaceutical formulations can further include one or more additives including, but not limited to, salts, chelating agents, preservatives, antimicrobials, surfactants, pH adjusters, and sterile water. Some exemplary additives can include glycerol and oleic acid. In some embodiments, the water phase of the emulsion formulations comprises normal saline. In another exemplary embodiment, the emulsion formulation includes disodium edetate (EDTA). In another exemplary embodiment, the emulsion formulation includes benzethonium chloride. In another exemplary embodiment, the emulsion formulation includes sodium hydroxide. In some embodiments, the formulation can be adjusted for tonicity with, but not limited to, dextrose, dextrose anhydrous, glycerol, mannitol, sodium chloride, potassium chloride, or other suitable tonicity agent.

In some embodiments, the pharmaceutical formulations can further include one or more surfactants. Exemplary surfactants include, but are not limited to, phosphatides, fatty acid esters, fatty acid alcohols, and combinations thereof. In some embodiments, the pharmaceutical formulations include about 0.2% (w/v) to about 1.0% (w/v) phosphatides as a surfactant. In some embodiments, the pharmaceutical formulations include about 3.0% (w/v) to about 6.0% (w/v) surfactant. In some embodiments, the pharmaceutical formulations include glycerol or oleic acid.

The present disclosure further provides a method of making pharmaceutical formulations comprising ketamine and propofol. In some embodiments, the method of making comprises dissolving ketamine, such as free base ketamine, in an oil phase to produce an emulsion formulation comprising ketamine and propofol. The method can further comprise dissolving propofol in the oil phase. In some embodiments, the propofol is dissolved in, or already present in a lipid, such as soybean oil, prior to dissolving the ketamine in the oil phase. In other embodiments, the ketamine is first dissolved in a lipid of the oil phase before the propofol is dissolved in the oil phase. In further embodiments, the ketamine and propofol can be dissolved in the oil phase together or simultaneously. In some embodiments of the method, the oil phase into which the ketamine is dissolved comprises soybean oil and propofol. The method can further comprise adding water, saline, and/or a surfactant or other additive as described herein to the formulation. It will be recognized that any of the above-described additives can be added at any time during the above method steps.

Also provided herein is a pharmaceutical formulation comprising ketamine and propofol made by the processes described herein.

The present disclosure further provides a method of delivering the pharmaceutical formulations described herein, comprising injecting the formulation into a subject. The injection can be, e.g., intravenous.

Also provided herein is a method of providing sedation, amnesia, analgesia, anxiolysis, hemodynamic stability, or combinations thereof to a subject in need thereof comprising administering a pharmaceutical formulation as described herein to the subject.

"Hemodynamic stability" as used herein means that a subject has a stable blood pressure and consistent flow of blood through the subject's body.

The formulations disclosed herein can also be used in combination with other therapies, such as intubation, procedural sedation, or continuous sedation to maintain an anesthetic state. The present formulations can be administered to subjects requiring sedation for procedures in a hospital emergency department, intensive care unit, or operating room.

The methods provided herein can be performed on any suitable subject. Suitable subjects can include animals such as humans, non-human primates, rodents, dogs, cats, horses, pigs, sheep, goats, cows, or other mammals.

In some embodiments of the methods disclosed herein, the formulations can be administered, for example, from a single dose to multiple doses. The precise amount of ketamine and propofol in the formulations that will be therapeutically effective in the methods provided herein, and the dosing regimen, for example, will vary according to factors known in the art including the size and biological state of the subject, the species to which the formulation is being administered, the dosing regimen selected, the application site, the particular formulation, the therapeutic effect being sought, and the condition being treated. Those of ordinary skill in the art can readily determine appropriate formulations, therapeutically effective amounts of ketamine and propofol, and dosing regimens based on the guidance provided herein, information available in the art pertaining to ketamine and propofol, and routine testing.

In some embodiments of the methods disclosed herein, the formulations can be administered for induction of anesthesia, infusion, maintenance of anesthesia, and sedation. The ratio of ketamine to propofol in the formulations described herein can range from about 1:4 to about 2:1, depending on the subject's health condition (e.g., critically ill, nearly comatose, healthy, etc.), body size and type, and the desired anesthetic effect. A skilled anesthetist and/or physician can adjust the dose to achieve the desired effect in a particular subject in accordance with the conventional skill in the art.

In some embodiments of the methods disclosed herein, the formulations can be administered for induction of anesthesia. The ketamine and propofol can each be present in a range of concentrations for induction, with lower limits based on minimum therapeutic potency of the ketamine or propofol, and upper limits based primarily on solubility and/or safety of each of the drugs. The ratio of ketamine to propofol in the formulations described herein can range from about 1:4 to about 2:1. In some embodiments of the formulations administered for induction of anesthesia, the ratio of ketamine to propofol can range from about 1:4 to about 1:1. In some embodiments, the ratio of ketamine to propofol for induction is about 1:1.

In some exemplary embodiments for induction in a subject, an exemplary dose can include from about 0.1 mg/kg to about 8 mg/kg, from about 0.2 mg/kg to about 5 mg/kg, from about 0.2 mg/kg to about 2.5 mg/kg, from about 0.2 mg/kg to about 1.5 mg/kg, from about 0.2 mg/kg to about 1 mg/kg, from about 0.2 mg/kg to about 0.8 mg/kg, from about 0.2 mg/kg to about 0.5 mg/kg, from about 0.1 mg/kg to about 0.8 mg/kg, from about 0.1 mg/kg to about 0.5 mg/kg, from about 0.2 mg/kg to about 0.4 mg/kg, from about 0.2 mg/kg to about 0.3 mg/kg, about 0.2 mg/kg, or about 0.3 mg/kg, or about 0.25 mg/kg, about 0.1 mg/kg, about 0.2 mg/kg, about 0.8 mg/kg, or about 0.5 mg/kg of ketamine/propofol (1%). In some exemplary embodiments for induction in a subject, an exemplary dose can include from about 0.1 mg/kg to about 8 mg/kg, 0.2 mg/kg to about 5 mg/kg, from about 0.2 mg/kg to about 2.5 mg/kg, from about 0.2 mg/kg to about 1.5 mg/kg, from about 0.2 mg/kg to about 1 mg/kg, from about 0.2 mg/kg to about 0.8 mg/kg, from about 0.2 mg/kg to about 0.5 mg/kg, about 0.2 mg/kg, about 0.8 mg/kg, or about 0.5 mg/kg of ketamine; and 0.1 mg/kg to about 8 mg/kg, from about 0.2 mg/kg to about 5 mg/kg, from about 0.2 mg/kg to about 2.5 mg/kg, from about 0.2 mg/kg to about 1.5 mg/kg, from about 0.2 mg/kg to about 1 mg/kg, from about 0.2 mg/kg to about 0.8 mg/kg, from about 0.2 mg/kg to about 0.5 mg/kg, about 0.2 mg/kg, about 0.8 mg/kg, or about 0.5 mg/kg of propofol. In some embodiments, for induction in a subject, an exemplary formulation can have a concentration of about 5 mg/ml ketamine and about 5 mg/ml propofol. In some embodiments, for induction in a subject, subjects ranging from about 15 kg to about 160 kg may be treated. In some embodiments, for induction in a subject, total dosages delivered to a subject can range from about 5 mg of ketamine to about 130 mg of ketamine, from about 7 mg of ketamine to about 85 mg of ketamine, from about 7.5 mg of ketamine to about 80 mg of ketamine, from about 30 mg of ketamine to about 80 mg of ketamine, from about 7.5 mg of ketamine to about 130 mg of ketamine, from about 10 mg of ketamine to about 125 mg of ketamine, from about 11.25 mg of ketamine to about 120 mg of ketamine, or from about 10 mg of ketamine to about 100 mg of ketamine; and from about 5 mg of propofol to about 130 mg of propofol, from about 7 mg of propofol to about 85 mg of propofol, from about 7.5 mg of propofol to about 80 mg of propofol, from about 30 mg of propofol to about 80 mg of propofol, from about 7.5 mg of propofol to about 130 mg of propofol, from about 10 mg of propofol to about 125 mg of propofol, from about 11.25 mg of propofol to about 120 mg of propofol, or from about 10 mg of propofol to about 100 mg of propofol. In some embodiments, the subject can be an adult human patient. In some embodiments, the subject can be a pediatric human patient.

In some embodiments of the methods disclosed herein, the formulations can be administered for induction of anesthesia in a critically ill subject. As used herein, a "critically ill subject" includes a subject whose condition or conditions are life-threatening or a subject who requires comprehensive care and constant monitoring, usually in intensive care units and operating rooms, or any subject who needs a definitive airway or breathing tube placement with constant monitoring and comprehensive care. In some exemplary embodiments for induction in a critically ill subject, an exemplary dose can include from about 0.2 mg/kg to about 5 mg/kg, from about 0.2 mg/kg to about 2.5 mg/kg, from about 0.2 mg/kg to about 1.5 mg/kg, from about 0.2 mg/kg to about 1 mg/kg, from about 0.2 mg/kg to about 0.8 mg/kg, from about 0.2 mg/kg to about 0.5 mg/kg, about 0.2 mg/kg, about 0.8 mg/kg, or about 0.5 mg/kg of ketamine/propofol (1%). In some embodiments, for induction of anesthesia and/or sedation for critically ill patient, an exemplary dose can include from about 0.5 mg/kg to about 1 mg/kg of ketamine/propofol (1%). In some exemplary embodiments for induction in a critically ill subject, an exemplary dose can include from about 0.2 mg/kg to about 5 mg/kg, from about 0.2 mg/kg to about 2.5 mg/kg, from about 0.2 mg/kg to about 1.5 mg/kg, from about 0.2 mg/kg to about 1 mg/kg, from about 0.2 mg/kg to about 0.8 mg/kg, from about 0.2 mg/kg to about 0.5 mg/kg, about 0.2 mg/kg, about 0.8 mg/kg, or about 0.5 mg/kg of ketamine; and from about 0.2 mg/kg to about 5 mg/kg, from about 0.2 mg/kg to about 2.5 mg/kg, from about 0.2 mg/kg to about 1.5 mg/kg, from about 0.2 mg/kg to about 1 mg/kg, from about 0.2 mg/kg to about 0.8 mg/kg, from about 0.2 mg/kg to about 0.5 mg/kg, about 0.2 mg/kg, about 0.8 mg/kg, or about 0.5 mg/kg of propofol. In some embodiments, for induction in a critically ill subject, an exemplary formulation can have a concentration of about 5 mg/ml ketamine and about 5 mg/ml propofol. In some embodiments, for induction in a critically ill subject, subjects ranging from about 15 kg to about 160 kg may be treated. In some embodiments, for induction in a critically ill subject, total dosages delivered to a subject can range from about 7 mg of ketamine to about 85 mg of ketamine, from about 7.5 mg of ketamine to about 80 mg of ketamine, or from about 30 mg of ketamine to about 80 mg of ketamine; and 7 mg of propofol to about 85 mg of propofol, from about 7.5 mg of propofol to about 80 mg of propofol, or from about 30 mg of propofol to about 80 mg of propofol. In some embodiments, for induction in a critically ill subject that is nearly comatose, the dosage can be reduced to from about 0.1 mg/kg to about 0.8 mg/kg, from about 0.1 mg/kg to about 0.5 mg/kg, from about 0.2 mg/kg to about 0.4 mg/kg, from about 0.2 mg/kg to about 0.3 mg/kg, about 0.2 mg/kg, or about 0.3 mg/kg, or about 0.25 mg/kg. In some embodiments, the subject can be an adult human patient. In some embodiments, the subject can be a pediatric human patient.

In some embodiments of the methods disclosed herein, the formulations can be administered for induction of anesthesia in a subject having elective surgery. As used herein, a "subject having elective surgery" includes a subject having a scheduled surgery that does not involve a medical emergency. In some exemplary embodiments for induction in a subject having elective surgery, an exemplary dose can include from about 0.2 mg/kg to about 5 mg/kg, from about 0.2 mg/kg to about 2.5 mg/kg, from about 0.2 mg/kg to about 1.5 mg/kg, from about 0.2 mg/kg to about 1 mg/kg, from about 0.2 mg/kg to about 0.8 mg/kg, from about 0.2 mg/kg to about 0.5 mg/kg, about 0.2 mg/kg, about 0.8 mg/kg, or about 0.5 mg/kg of ketamine/propofol (1%). In some embodiments, for induction of anesthesia and/or sedation for a subject having elective surgery, an exemplary dose can include from about 0.75 mg/kg to about 1.5 mg/kg of ketamine/propofol (1%). In some exemplary embodiments for induction in a subject having elective surgery, an exemplary dose can include from about 0.2 mg/kg to about 5 mg/kg, from about 0.2 mg/kg to about 2.5 mg/kg, from about 0.2 mg/kg to about 1.5 mg/kg, from about 0.2 mg/kg to about 1 mg/kg, from about 0.2 mg/kg to about 0.8 mg/kg, from about 0.2 mg/kg to about 0.5 mg/kg, about 0.2 mg/kg, about 0.8 mg/kg, or about 0.5 mg/kg of ketamine; and from about 0.2 mg/kg to about 5 mg/kg, from about 0.2 mg/kg to about 2.5 mg/kg, from about 0.2 mg/kg to about 1.5 mg/kg, from about 0.2 mg/kg to about 1 mg/kg, from about 0.2 mg/kg to about 0.8 mg/kg, from about 0.2 mg/kg to about 0.5 mg/kg, about 0.2 mg/kg, about 0.8 mg/kg, or about 0.5 mg/kg of propofol. In some embodiments, for induction in a subject having elective surgery, an exemplary formulation can have a concentration of about 5 mg/ml ketamine and about 5 mg/ml propofol. In some embodiments, for induction in a subject having elective surgery, subjects ranging from about 15 kg to about 160 kg may be treated. In some embodiments, for induction in a subject having elective surgery, total dosages delivered to a subject can range from about 7.5 mg of ketamine to about 130 mg of ketamine, from about 10 mg of ketamine to about 125 mg of ketamine, from about 11.25 mg of ketamine to about 120 mg of ketamine, or from about 10 mg of ketamine to about 100 mg of ketamine; and from about 7.5 mg of propofol to about 130 mg of propofol, from about 10 mg of propofol to about 125 mg of propofol, from about 11.25 mg of propofol to about 120 mg of propofol, or from about 10 mg of propofol to about 100 mg of propofol. In some embodiments, the subject can be an adult human patient. In some embodiments, the subject can be a pediatric human patient.

In some embodiments of the methods disclosed herein, the formulations can be administered for infusion or maintenance of anesthesia. In some exemplary embodiments, a smart pump may be used to deliver the infusion dosage. The ketamine and propofol can each be present in a range of concentrations for infusion, with lower limits based on minimum therapeutic potency of the ketamine or propofol, and upper limits based primarily on solubility and/or safety of each of the drugs. The ratio of ketamine to propofol in the formulations described herein can range from about 1:4 to about 2:1. In some embodiments of the formulations administered for infusion of anesthesia, the ratio of ketamine to propofol can range from about 1:4 to about 1:1. In some embodiments, the ratio of ketamine to propofol for infusion is about 1:1, about 1:3, or about 1:4. In some exemplary embodiments, the ratio of ketamine to propofol for infusion in a critically ill subject is 1:3. In some exemplary embodiments, the ratio of ketamine to propofol for infusion in a subject having elective surgery is 1:4.

In some exemplary embodiments for infusion in a subject, exemplary dosage ranges of ketamine in the ketamine/propofol formulation can include from about 5 µg/kg per minute to about 16 µg/kg per minute, from about 5.56 µg/kg per minute to about 15.7 µg/kg per minute, from about 5 µg/kg per minute to about 10 µg/kg per minute, from about 5 µg/kg per minute to about 8 µg/kg per minute, from about 5 µg/kg per minute to about 12 µg/kg per minute, 5 µg/kg per minute, 6 µg/kg per minute, or about 10 µg/kg per minute of ketamine. In some exemplary embodiments for infusion in a subject, exemplary dosage ranges of propofol in the ketamine/propofol formulation can include from about 5 µg/kg per minute to about 16 µg/kg per minute, from about 5.56 µg/kg per minute to about 15.7 µg/kg per minute, from about 5 µg/kg per minute to about 10 µg/kg per minute, from about 5 µg/kg per minute to about 8 µg/kg per minute, from about 5 µg/kg per minute to about 12 µg/kg per minute, 5 µg/kg per minute, 6 µg/kg per minute, or about 10 µg/kg per minute of propofol. In some embodiments, for infusion, a 1:3, 1:4, or 1:1 ketamine/propofol formulation can be delivered to a subject by a smart pump at a rate of from about 0.5 ml per hour to about 40 ml per hour, from about 1 ml per hour to about 30 ml per hour, from about 2 ml per hour to about 20 ml per hour, or from about 3 ml per hour to about 15 ml per hour to subjects ranging from about 15 kg to about 160 kg. In some embodiments, for infusion in a subject, dosages delivered to a subject can range from about 80 µg per minute to about 2700 µg per minute, from about 83.3 µg per minute to about 2500 µg per minute, from about 85 µg per minute to about 2000 µg per minute, from about 85 µg per minute to about 1800 µg per minute, or from about 83 µg per minute to about 1500 µg per minute of ketamine. In some embodiments, for infusion in a subject, dosages delivered to a subject can range from about 80 µg per minute to about 2700 µg per minute, from about 83.3 µg per minute to about 2500 µg per minute, from about 85 µg per minute to about 2000 µg per minute, from about 85 µg per minute to about 1800 µg per minute, or from about 83 µg per minute to about 1500 µg per minute of propofol.

In some exemplary embodiments for infusion in a critically ill subject or a subject having elective surgery, exemplary dosage ranges of ketamine in the ketamine/propofol formulation can include from about 5 µg/kg per minute to about 16 µg/kg per minute, from about 5.56 µg/kg per minute to about 15.7 µg/kg per minute, from about 5 µg/kg per minute to about 10 µg/kg per minute, from about 5 µg/kg per minute to about 8 µg/kg per minute, from about 5 µg/kg per minute to about 12 µg/kg per minute, 5 µg/kg per minute, 6 µg/kg per minute, or about 10 µg/kg per minute of ketamine. In some exemplary embodiments for infusion in a critically ill subject or a subject having elective surgery, exemplary dosage ranges of propofol in the ketamine/propofol formulation can include from about 5 µg/kg per minute to about 16 µg/kg per minute, from about 5.56 µg/kg per minute to about 15.7 µg/kg per minute, from about 5 µg/kg per minute to about 10 µg/kg per minute, from about 5 µg/kg per minute to about 8 µg/kg per minute, from about 5 µg/kg per minute to about 12 µg/kg per minute, 5 µg/kg per minute, 6 µg/kg per minute, or about 10 µg/kg per minute of propofol. In some embodiments, for infusion, a 1:3, 1:4, or 1:1 ketamine/propofol formulation can be delivered to a critically ill subject or a subject having elective surgery by a smart pump at a rate of from about 0.5 ml per hour to about 40 ml per hour, from about 1 ml per hour to about 30 ml per hour, from about 2 ml per hour to about 20 ml per hour, or from about 3 ml per hour to about 15 ml per hour to critically ill or elective surgery subjects ranging from about 15 kg to about 160 kg. In some embodiments, for infusion in a critically ill or elective surgery subject, dosages delivered to a subject can range from about 80 µg per minute to about 2700 µg per minute, from about 83.3 µg per minute to about 2500 µg per minute, from about 85 µg per minute to about 2000 µg per minute, from about 85 µg per minute to about 1800 µg per minute, or from about 83 µg per minute to about 1500 µg per minute of ketamine. In some embodiments, for infusion in a critically ill or elective surgery subject, dosages delivered to a subject can range from about 80 µg per minute to about 2700 µg per minute, from about 83.3 µg per minute to about 2500 µg per minute, from about 85 µg per minute to about 2000 µg per minute, from about 85 µg per minute to about 1800 µg per minute, or from about 83 µg per minute to about 1500 µg per minute of propofol.

A number of embodiments of the invention have been described. Nevertheless, it will be understood that various modifications can be made without departing from the spirit and scope of the invention. For example, different amounts of ketamine, propofol, and lipid can be used, as well as different forms of ketamine or propofol that allow substantial dissolution in the oil phase. Accordingly, other embodiments are within the scope of the following claims.

EXAMPLES

Unless noted otherwise, all reagents were obtained from commercial suppliers. Unless noted otherwise, appropriate laboratory, medical, and analytical procedures were employed.

Example 1

Surgical Pain Control and Other Effects Using Propofol or Ketamine/Propofol ("Ketofol")

85 patients of ASA Class 1-2 scheduled for surgical procedures that involved general anesthesia were assigned to one of two arms, one involving induction with propofol and the other involving induction with "ketofol" (a ketamine/propofol combination) in a randomized, double-blinded controlled trial. Patients were placed on standard ASA monitors including a BIS monitor and a noninvasive cardiac output monitor (NICOM) prior to induction of general anesthesia.

One minute before induction, baseline hemodynamics were recorded with standard ASA monitors as well as with the NICOM. Providers were given one 20 ml syringe and one 10 ml syringe for rescue if needed. As part of the induction, fentanyl (1-2 mcg/kg) and any relaxant excluding succinylcholine and pancuronium was given. The 20 ml syringe in both groups looked identical, appeared to be propofol but depending on the group they were randomized to, it represented either 2 mg/kg of propofol (propofol group) or 0.75 mg/kg of ketamine and 1.5 mg/kg of propofol ("ketofol" group). The 10 ml rescue syringe, if used, represented 1 mg/kg of propofol (propofol group) or 0.25 mg/kg of ketamine and 0.5 mg/kg of propofol ("ketofol" group). Hemodynamics were recorded every minute for a total of 30 minutes post-induction. During this time, anesthesia was maintained with any volatile agent excluding nitrous oxide. This study did not restrict any use or amount of anti-emetics allowed nor were there any restrictions on additional narcotics given after the induction period. Patients were given survey questions that centered on emergence, discharge times, pain control, and nausea/vomiting. In addition, nurses were also asked to fill out a survey which dealt with similar questions. Results of the Surveys are reported in Table 1.

Of note, there was a trend towards improved pain control in the "ketofol" group as compared to the propofol group. Among the other variables observed, no significant difference was seen in post-operative nausea and/or vomiting scores, anti-emetic and narcotic use either in the operating room or recovery, or in use of protection (use of anti-emetics in operating room) from postoperative nausea and vomiting scores from nursing responses in the propofol and "ketofol" groups.

TABLE 1

Nursing and Patient Assessment

| Nursing Assessment | Propofol(N = 40) | | Ketofol(N = 39) | | Comparison | | |
|---|---|---|---|---|---|---|---|
| | Mean | SD | Mean | SD | Difference | 95% CI | p-value |
| Experience (years) | 2.7 | 2.0 | 2.5 | 1.8 | 0.2 | (−0.6, 1.0) | .62 |
| Emergence (wake up) | 5.4 | 1.6 | 5.6 | 1.1 | −0.2 | (−0.8, 0.4) | .47 |
| Discharge (from unit) | 5.1 | 1.5 | 4.7 | 1.5 | 0.4 | (−0.3, 1.1) | .25 |
| Protection from PONV | 5.5 | 2.1 | 5.4 | 1.8 | 0.0 | (−0.8, 0.9) | .97 |

Likert scaled responses from 0 (very poorly) to 7 (perfectly).

| Patient Assessment | Propofel(N = 40) | | Ketofol(N = 39) | | Comparison | | |
|---|---|---|---|---|---|---|---|
| | Mean | SD | Mean | SD | Difference | 95% CI | p-value |
| Emergence (woke up well) | 5.5 | 1.5 | 5.6 | 1.4 | −0.1 | (−0.8, 0.5) | .67 |
| No PONV | 5.5 | 2.0 | 5.2 | 2.1 | 0.4 | (−0.5, 1.3) | .4 |
| No Pain | 3.8 | 1.5 | 4.3 | 1.7 | −0.5 | (−1.2, 0.3) | .22 |

Likert scaled responses from 0 (strongly disagree) to 7 (strongly agree).
PONV = Post-operative nausea/vomiting

Example 2

Ketamine/Propofol Admixture "Ketofol" vs Etomidate for Intubation in the Critically Ill A single center, multi units, stratified, randomized, parallel-group clinical trial of adult critically ill patients admitted to a medical, surgical, or transplant/oncologic unit was performed. A total of 160 patients who needed emergent intubations were randomly assigned to receive either "ketofol" or etomidate to facilitate endotracheal intubation. Eight patients subsequently withdrew consent, leaving 152 in the trial. Of those patients, 79 received "ketofol" and 73 received etomidate. Stratification was based on shock status (mean arterial pressure 65 mmHg) and unit type. The primary outcome was the change in mean arterial pressure from baseline over the first 5 minutes following drug administration. Secondary outcomes were new-onset vasopressor use, narcotic use, intubation difficulty score, new-onset delirium, transfusions, ventilator free days, ICU free days, and hospital mortality.

There was no clinical or statistical difference in the change of mean arterial pressure from baseline at 5, 10 and 15 minutes post drug administration. There was also no statistical difference in the use of new-onset immediate or delayed vasopressors between groups. The etomidate group required significantly more non-RBC transfusions than the "ketofol" group [non-red blood cell: 22% (16) vs. 10% (8), P=0.046; red blood cell: 29% (21) vs. 16% (13), P=0.069]. There was no difference in all other secondary outcomes including intubation complications, hospital mortality, length of stay, and new onset delirium. Serious adverse events were reported in 3% of the "ketofol" group and in 5% of the etomidate group. In this heterogeneous population of critical care patients, "ketofol" and etomidate were similar with regards to peri-intubation hemodynamic stability.

Example 3

Preparation of Long-Term Stable Propofol-Ketamine Emulsions 2,6-diisopropylphenol (propofol) and soybean oil were obtained from Sigma-Aldrich (St. Louis, Mo., USA). Egg lecithin was purchased from Millipore Sigma (Burlington, Mass., USA). Glycerol was supplied by Fisher Scientific. Ketamine free base was prepared from ketamine hydrochloride using $NaHCO_3$ and analyzed by $^1H$ NMR and HPLC. More specifically, ketamine free base was prepared using commercially available Ketamine hydrochloride: 3 ml Ketamine hydrochloride solution (100 mg/ml) was diluted with deionized water (20 ml) in a 50 ml round bottom flask and cooled to 0° C. in an ice bath. While stirring, 2N NaHCO3 was added drop wise to the diluted solution and the pH change was monitored. When the pH was reached to 8.4, white precipitate was observed. The precipitate was extracted with ethyl acetate and the organic layer was dried with excess sodium sulfate, concentrated on rotary evaporator.

60-Second Sonication Emulsions

Propofol-ketamine free base emulsion was formulated as propofol 10 mg (1% w/v), ketamine free base 10 mg (1% w/v), soybean oil 100 mg (10% w/v), glycerol 22.5 mg (2.25% w/v), egg lecithin 12 mg (1.2% w/v) and EDTA 0.005% with deionized (DI) water to a volume of 1 ml. The pH was adjusted to 7.4 using sodium hydroxide.

Briefly, propofol and ketamine free base were dispersed in a mixture of soybean oil, glycerol and egg lecithin. A defined volume of DI water was added to the dispersion and then the mixture was emulsified with a tip sonicator (Misonix Sonicator 3000) on ice bath at 18 W for 1 min.

To determine the emulsion droplet size and zeta potential, shown in Table 2, the emulsion was dispersed in deionized water and analyzed using dynamic light scattering (Delsa Nano C, Beckmann Coulter, Calif., USA).

TABLE 2

Zeta size and potential of the propofol and ketamine free base emulsion droplets.

| | Size (nm) | Polydispersity Index (PI) | Zeta potential (mV) |
|---|---|---|---|
| Day 0 | 364.4 | 0.204 | −49.85 |
| Day 3 | 361.3 | 0.236 | — |
| Day 7 | 347.4 | 0.253 | — |
| Day 14 | 523.6 | 0.055 | — |
| Day 70 | 379.7 | 0.173 | — |
| Day 82 | 369.5 | 0.245 | −44.16 |
| Day 88 | 365.9 | 0.168 | −41.9 |
| Day 97 | 310.7 | 0.215 | −44.87 |
| Day 163 | 368.1 | 0.191 | −41.39 |

75-Second Sonication Emulsions

Propofol-ketamine free base emulsion was formulated as propofol 5 mg (0.5% w/v) and ketamine free base 5 mg (0.5% w/v), or propofol 10 mg (1% w/v) and ketamine free base 10 mg (1% w/v), soybean oil 100 mg (10% w/v), glycerol 22.5 mg (2.25% w/v), egg lecithin 12 mg (1.2% w/v) and EDTA 0.005% with deionized (DI) water to a volume of 1 ml. The pH was adjusted to 7.4 using sodium hydroxide.

Briefly, propofol and ketamine free base were dispersed in a mixture of soybean oil, glycerol and egg lecithin. A defined volume of DI water was added to the dispersion and then the mixture was emulsified with a tip sonicator (Misonix Sonicator 3000) on ice bath at 18 W for 75 seconds.

Emulsions were stored at room temperature or 4° C. To determine the emulsion droplet size and zeta potential, shown in Table 3 for room temperature storage and Table 4 for 4° C., the emulsion was dispersed in deionized water and analyzed using dynamic light scattering (Delsa Nano C, Beckmann Coulter, Calif., USA). The increased sonication time slightly decreased droplet sizes but did not impact stability of the emulsion stored at room temperature or 4° C.

TABLE 3

Zeta size and potential of the propofol and ketamine free base emulsion droplets (formulations stored at room temperature)

| | 0.5% Propofol + 0.5% Ketamine free base | | 1% Propofol + 1% Ketamine free base | |
|---|---|---|---|---|
| | Size in nm (PDI) | Zeta potential in mV | Size in nm (PDI) | Zeta potential in mV |
| Day 0 | 315 (0.296) | −38.3 | 215 (0.244) | −45.2 |
| Day 3 | 240 (0.245) | −45.0 | 256 (0.222) | −39.3 |
| Day 7 | 238 (0.214) | −39.7 | 254 (0.242) | −47.9 |
| Day 12 | 238 (0.192) | −43.7 | 248 (0.207) | −49.54 |
| Day 17 | 240 (0.207) | −49.2 | 244 (0.215) | −51.9 |
| Day 26 | 235 (0.177) | −54.6 | 251 (0.195) | −61.9 |
| Day 45 | 238 (0.238) | — | 243 (0.179) | −56.2 |
| Day 66 | 242 (0.166) | −51.3 | 402 (0.308) | −57.9 |

TABLE 4

Zeta size and potential of the propofol and ketamine free base emulsion droplets (formulations stored at 4° C.).

| | 0.5% Propofol + 0.5% Ketamine free base | | 1% Propofol + 1% Ketamine free base | |
|---|---|---|---|---|
| | Size in nm (PDI) | Zeta potential in mV | Size in nm (PDI) | Zeta potential in mV |
| Day 0 | 237 (0.210) | −38.3 | 266 (0.238) | −41.9 |
| Day 3 | 252 (0.184) | −47.1 | 272 (0.228) | −42.6 |
| Day 7 | 247 (0.213) | −47.7 | 273 (0.231) | −30.9 |
| Day 12 | 247 (0.209) | −47.5 | 272 (0.192) | −46.0 |
| Day 17 | 247 (0.210) | −49.7 | 265 (0.233) | −46.3 |
| Day 26 | 242 (0.229) | −47.1 | 268 (0.200) | −58.1 |
| Day 45 | 239 (0.214) | — | 269 (0.213) | −56.3 |
| Day 66 | 237 (0.175) | −51.6 | 262 (0.248) | −56.2 |

EXEMPLARY EMBODIMENTS

Some exemplary embodiments are described in paragraphs [01] to [61] below.

[01] A pharmaceutical formulation, comprising:
ketamine;
propofol; and
a lipid, wherein the ketamine is substantially dissolved in the lipid.

[02] The pharmaceutical formulation of the embodiment of paragraph [01], wherein the formulation is an oil-in-water emulsion.

[03] The pharmaceutical formulation of any one of the embodiments of paragraphs [01]-[02], wherein the formulation is essentially free of chloride ions.

[04] The pharmaceutical formulation of any one of the embodiments of paragraphs [01]-[03], wherein the formulation comprises from about 2.5% (w/v) to about 20% (w/v) lipid.

[05] The pharmaceutical formulation of any one of the embodiments of paragraphs [01]-[04], wherein the formulation comprises about 10% (w/v) lipid.

[06] The pharmaceutical formulation of any one of the embodiments of paragraphs [01]-[05], wherein the ketamine is present in a concentration of from about 1 mg/ml to about 10 mg/ml.

[07] The pharmaceutical formulation of any one of the embodiments of paragraphs [01]-[06], wherein the propofol is present in a concentration of from about 1 mg/ml to about 10 mg/ml.

[08] The pharmaceutical formulation of any one of the embodiments of paragraphs [01]-[05], wherein the ketamine is present in a concentration of from about 2 mg/ml to about 5 mg/ml.

[09] The pharmaceutical formulation of any one of the embodiments of paragraphs [01]-[06], wherein the propofol is present in a concentration of from about 5 mg/ml to about 8 mg/ml.

[10] The pharmaceutical formulation of any one of the embodiments of paragraphs [01]-[05], wherein the ketamine is present in a concentration of from about 1 mg/ml to about 10 mg/ml, and the propofol is present in a concentration of from about 1 mg/ml to about 10 mg/ml.

[11] The pharmaceutical formulation of any one of the embodiments of paragraphs [01]-[05], wherein the ketamine is present in a concentration of from about 2 mg/ml to about 5 mg/ml and the propofol is present in a concentration of from about 5 mg/ml to about 8 mg/ml.

[12] The pharmaceutical formulation of any one of the embodiments of paragraphs [01]-[11], wherein the ratio of ketamine to propofol is from about 1:4 to about 2:1.

[13] The pharmaceutical formulation of any one of the embodiments of paragraphs [01]-[11], wherein the ratio of ketamine to propofol is from about 1:4 to about 1:1.

[14] The pharmaceutical formulation of any one of the embodiments of paragraphs [01]-[11], wherein the ratio of ketamine to propofol is selected from about 1:4, about 1:3, about 1:2, and about 1:1.

[15] The pharmaceutical formulation of any one of the embodiments of paragraphs [01]-[05], wherein the ketamine is present in a concentration of about 5 mg/ml and the propofol is present in a concentration of about 5 mg/ml.

[16] The pharmaceutical formulation of any one of the embodiments of paragraphs [01]-[05], wherein the ketamine is present in a concentration of about 3.3 mg/ml and the propofol is present in a concentration of about 6.6 mg/ml.

[17] The pharmaceutical formulation of any one of the embodiments of paragraphs [01]-[05], wherein the ketamine is present in a concentration of about 2.5 mg/ml and the propofol is present in a concentration of about 7.5 mg/ml.

[18] The pharmaceutical formulation of any one of the embodiments of paragraphs [01]-[05], wherein the ketamine is present in a concentration of about 2 mg/ml and the propofol is present in a concentration of about 8 mg/ml.

[19] The pharmaceutical formulation of any one of the embodiments of paragraphs [01]-[18], wherein the lipid is selected from soybean oil, purified egg phospholipid, oleic acid, glyceryl ester and mixtures thereof.

[20] The pharmaceutical formulation of any one of the embodiments of paragraphs [01]-[18], wherein the lipid is soybean oil.

[21] The pharmaceutical formulation of any one of the embodiments of paragraphs [01]-[20], wherein the formulation is an emulsion and maintains phase stability for at least two years.

[22] A method of manufacturing a pharmaceutical formulation comprising ketamine and propofol, the method comprising dissolving ketamine in an oil phase to produce an emulsion formulation comprising ketamine and propofol.

[23] The method of the embodiment of paragraph [22], wherein the ketamine is free base ketamine.

[24] The method of any one of the embodiments of paragraphs [22]-[23], wherein the propofol is present in the oil phase prior to the dissolving the ketamine in the oil phase.

[25] The method any one of the embodiments of paragraphs [22]-[24], further comprising dissolving the propofol in the oil phase.

[26] The method of the embodiment of paragraph [25], wherein ketamine is dissolved in the oil phase prior to the dissolving the propofol in the oil phase.

[27] The method of any one of the embodiments of paragraphs [22]-[26], further comprising adding a surfactant.

[28] The method of any one of the embodiments of paragraphs [22]-[27], wherein the pharmaceutical formulation is essentially free of chloride ions.

[29] An oil-in-water emulsion comprising:
ketamine;
propofol; and
a lipid, wherein the emulsion is essentially free of chloride ions.

[30] The oil-in-water emulsion of the embodiment of paragraph [29], wherein the emulsion comprises about 10% (w/v) lipid.
[31] The oil-in-water emulsion of any one of the embodiments of paragraphs [29]-[30], wherein the ketamine is present in a concentration of from about 2 mg/ml to about 5 mg/ml.
[32] The oil-in-water emulsion of any one of the embodiments of paragraphs [29]-[31], wherein the propofol is present in a concentration of from about 5 mg/ml to about 8 mg/ml.
[33] A pharmaceutical composition prepared by the process comprising:
dissolving ketamine in an oil phase to produce an emulsion formulation comprising ketamine and propofol.
[34] The process of the embodiment of paragraph [33], wherein the ketamine is free base ketamine.
[35] The process of any one of the embodiments of paragraphs [33]-[34], wherein the propofol is present in the oil phase prior to the dissolving the ketamine in the oil phase.
[36] The process of any one of the embodiments of paragraphs [33]-[35], further comprising dissolving the propofol in the oil phase.
[37] The process of any one of the embodiments of paragraphs [33]-[36], further comprising adding a surfactant.
[38] The process of any one of the embodiments of paragraphs [33]-[37], wherein the pharmaceutical formulation is essentially free of chloride ions.
[39] A method of providing sedation, amnesia, analgesia, anxiolysis, hemodynamic stability, or combinations thereof to a subject in need comprising administering the pharmaceutical formulation of any one of the embodiments of paragraphs [01]-[21] to the subject.
[40] The method of the embodiment of paragraph [39], wherein administering comprises injecting the formulation into the subject.
[41] The method of any one of the embodiments of paragraphs [39]-[40], wherein administering comprises delivering a dose of from about 0.1 mg/kg to about 8 mg/kg ketamine and from about 0.1 mg/kg to about 8 mg/kg propofol to a subject ranging from about 15 kg to about 160 kg.
[42] The method of any one of the embodiments of paragraphs [39]-[40], wherein the administering comprises delivering a dose of from about 7.5 mg of ketamine to about 80 mg of ketamine and from about 7.5 mg of propofol to about 80 mg of propofol to a critically ill subject.
[43] The method of any one of the embodiments of paragraphs [39]-[40], wherein the administering comprises delivering a dose of from about 11.25 mg of ketamine to about 120 mg of ketamine and from about 11.25 mg of propofol to about 120 mg of propofol to a subject having elective surgery.
[43] The method of any one of the embodiments of paragraphs [39]-[40], wherein the administering comprises delivering the formulation by a smart pump at a rate of from about 1 ml per hour to about 30 ml per hour and a dose of from about 83.3 µg per minute to about 2500 µg per minute.
[44] The pharmaceutical formulation of any one of the embodiments of paragraphs [01]-[21], wherein at least 70% of ketamine is present in the lipid.
[45] The pharmaceutical formulation of any one of the embodiments of paragraphs [01]-[21], wherein at least 80% of ketamine is present in the lipid.
[46] The pharmaceutical formulation of any one of the embodiments of paragraphs [01]-[21], wherein at least 90% of ketamine is present in the lipid.
[47] The pharmaceutical formulation of any one of the embodiments of paragraphs [01]-[21], wherein at least 95% of ketamine is present in the lipid.
[48] The pharmaceutical formulation of any one of the embodiments of paragraphs [01]-[21], wherein at least 97% of ketamine is present in the lipid.
[49] The pharmaceutical formulation of any one of the embodiments of paragraphs [01]-[21], wherein at least 99% of ketamine is present in the lipid.
[50] The pharmaceutical formulation of any one of the embodiments of paragraphs [01]-[21] and [45]-[49], wherein the pH of the formulation is about 7.0.
[51] The pharmaceutical formulation of any one of the embodiments of paragraphs [01]-[21] and [45]-[49], wherein the pH of the formulation is about 7.5.
[52] The pharmaceutical formulation of any one of the embodiments of paragraphs [01]-[21] and [45]-[49], wherein the pH of the formulation is about 8.0.
[53] The pharmaceutical formulation of any one of the embodiments of paragraphs [01]-[21] and [45]-[49], wherein the pH of the formulation is about 8.5.
[54] The pharmaceutical formulation of any one of the embodiments of paragraphs [01]-[21] and [45]-[53], wherein the pharmaceutical formulation has less than 0.02% (w/v) chloride ion.
[55] The pharmaceutical formulation of any one of the embodiments of paragraphs [01]-[21] and [45]-[53], wherein the pharmaceutical formulation has less than 0.01% (w/v) chloride ion.
[56] The pharmaceutical formulation of any one of the embodiments of paragraphs [01]-[21] and [45]-[53], wherein the pharmaceutical formulation has less than 0.005% (w/v) chloride ion.
[57] The pharmaceutical formulation of any one of the embodiments of paragraphs [01]-[21] and [45]-[53], wherein the pharmaceutical formulation has less than 0.001% (w/v) chloride ion.
[58] The process of any one of the embodiments of paragraphs [33]-[38], further comprising adjusting the pH of the composition to about 7.0.
[59] The process of any one of the embodiments of paragraphs [33]-[38], further comprising adjusting the pH of the composition to about 7.5.
[60] The process of any one of the embodiments of paragraphs [33]-[38], further comprising adjusting the pH of the composition to about 8.0.
[61] The process of any one of the embodiments of paragraphs [33]-[38], further comprising adjusting the pH of the composition to about 8.5.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A pharmaceutical formulation, comprising:
ketamine free base;
propofol; and a lipid, wherein the formulation is an oil-in-water emulsion and essentially free of chloride ions.

2. The pharmaceutical formulation of claim 1, wherein the formulation comprises from about 2.5% (w/v) to about 20% (w/v) lipid.

3. The pharmaceutical formulation of claim 1, wherein the ketamine is present in a concentration of from about 1 mg/ml to about 10 mg/ml.

4. The pharmaceutical formulation of claim 1, wherein the propofol is present in a concentration of from about 1 mg/ml to about 10 mg/ml.

5. The pharmaceutical formulation of claim 1, wherein the ketamine is present in a concentration of from about 2 mg/ml to about 5 mg/ml.

6. The pharmaceutical formulation of claim 1, wherein the propofol is present in a concentration of from about 5 mg/ml to about 8 mg/ml.

7. The pharmaceutical formulation of claim 1, wherein the ratio of ketamine to propofol is from about 1:4 to about 2:1.

8. The pharmaceutical formulation of claim 1, wherein the ketamine is present in a concentration of about 5 mg/ml and the propofol is present in a concentration of about 5 mg/ml.

9. The pharmaceutical formulation of claim 1, wherein the lipid is selected from soybean oil, purified egg phospholipid, oleic acid, and mixtures thereof.

10. The pharmaceutical formulation of claim 1, wherein the formulation is an emulsion and maintains phase stability for at least two years.

11. The pharmaceutical formulation of claim 1, wherein the lipid is glyceryl ester.

\* \* \* \* \*